United States Patent [19]

Lin et al.

[11] Patent Number: 4,939,139

[45] Date of Patent: Jul. 3, 1990

[54] 7-CHLORO-5,6-DIHYDRO-3-(5-(1,2-DIHYDROXY-ISOPROPYL)-1,2,4-OXADIAZOL-3-YL)-5-METHYL-6-OXO-4H-IMIDAZO[1,5A][1,4]BENZODIAZEPINE

[75] Inventors: Jiunn H. Lin, Ambler; Harri G. Ramjit; Steven M. Pitzenberger, both of Lansdale; Edgar H. Ulm, Green Lane, all of Pa.

[73] Assignee: Merck & Co., Inc., Rahway, N.J.

[21] Appl. No.: 385,040

[22] Filed: Jul. 26, 1989

[51] Int. Cl.$^5$ .................. C07D 521/00; A61K 31/55
[52] U.S. Cl. .................................... 514/220; 540/498
[58] Field of Search .................. 514/220; 540/498

[56] References Cited

U.S. PATENT DOCUMENTS 4,507,313 3/1985 Braestrup et al. .................. 514/220
4,775,671 10/1988 Hunkeler et al. .................. 514/220

*Primary Examiner*—Robert T. Bond
*Attorney, Agent, or Firm*—William H. Nicholson; Joseph F. DiPrima

[57] ABSTRACT

A metabolite of the known anxiolytic agent, 7-chloro-5,6-dihydro-3-(5-isopropyl-1,2,4-oxadiazol-3-yl)-5-methyl-6-oxo-4H-i midazo[1,5a][1,4]benzodiazepine is a 1,2-dihydroxy derivative of the isopropyl moiety and is itself an anxiolytic agent of greater activity than its substrate.

3 Claims, No Drawings

7-CHLORO-5,6-DIHYDRO-3-(5-(1,2-DIHYDROXY-ISOPROPYL)-1,2,4-OXADIAZOL-3-YL)-5-METHYL-6-OXO-4H-IMIDAZO[1,5A][1,4]BENZODIAZEPINE

SUMMARY OF THE INVENTION

This invention is concerned with the title compound of structural formula:

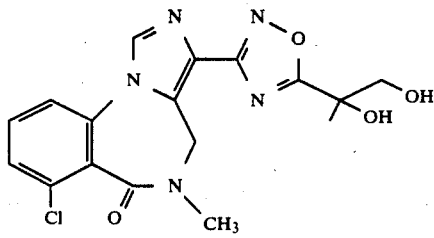

which is an anxiolytic agent. It was first discovered as a mammalian metabolite of the anxiolytic agent of structual formula:

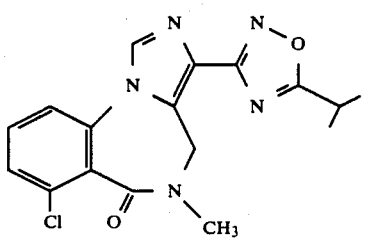

which is generically described in U.S. Pat. No. 4,507,313. The metabolite has since been synthesized and shown to be about three times as active as an anxiolytic as its substrate.

The invention is also concerned with a novel process for synthesis of the novel compound; pharmaceutical formulations thereof; and a method of treating anxiety therewith.

BACKGROUND OF THE INVENTION

The benzodiazepines have formed an important class of anxiolytic agents for several years. Recently there have been publications such as U.S. Pat. Nos. 4,507,313 and 4,775,671. On the sub-group of the class, known as the imidazobenzodiazepines, particularly in which the imidazo group is substituted with an alkyloxadiazole group.

Now with the present invention there is provided a dihydroxy derivative of an important member of that subgroup which is about three times as active as its parent as an anxiolytic agent. The potentiating effect of dihydroxylation was not previously expected.

DETAILED DESCRIPTION OF THE INVENTION

This invention is concerned with the novel compound of structural formula:

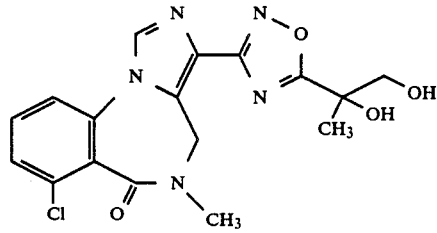

or pharmaceutically acceptable salt thereof.

This compound a metabolite of the above-identified substrate was isolated from the urine of laboratory animals, partially purified and analyzed by mass spectrometric techniques such as EI and FAB/MS. The results of these experiments are summarized in Table I.

The absolute identity of the compound was established from High Resolution Exact mass measurements summarized in Table II while hydroxylation was verified from the corresponding mass spectra of the trimethyl silyl ether derivative, also shown in Table I.

TABLE I

Molecular Weight Informatin Obtained by (a) Electron Ionization (EI)/MS and FAB/MS for the Parent Compound and Metabolite M3 (Analyzed as the Hydroxy and TMS Derivatives)

| Sample ID | 20 ev | 70 ev | FAB |
|---|---|---|---|
| Parent | $M^+ = 357$ | $M^+ = 357$ | $M + H = 358$ |
| Parent | | | 358.10690. |
| Metabolite | — | $M^+ = 389$ | $M + H = 390$ |
| Metabolite | — | — | 390.09650. |
| Metabolite-TMS | $M^+ = 533$ | — | $M + H = 534$ |

TABLE II

Illustration of Accurate Mass Measurement and Empirical Formula Established by FAB/MS Using an External Standard, for Parent and Metabolite

| Sample ID | Measured Mass (M + H) | Empirical Formula | Theoretical Mass |
|---|---|---|---|
| Parent | 358.10690 | $C_{17}H_{17}N_5O_2Cl$ | 358.10707773 |
| Metabolite | 390.09650 | $C_{17}H_{17}N_5O_4Cl$ | 390.0969070 |

The process for preparing the novel compound of this invention comprises hydrolyzing the corresponding 2,2,4-trimethyldioxolane with refluxing 80% acetic acid/acetone (v/v) for about 48 hours.

The novel pharmaceutical formulations of this invention comprising the novel compound as active ingredient are prepared by conventional pharmaceutical method for oral, parenteral or rectal administration and comprises from 0.05 to 100 mg of novel compound per unit dose.

The novel method of treatment of this invention comprises the administration of an effective anxiolytic amount of the novel compound to a patient in need of such treatment. An effective amount of comprises about 0.1 to 300 mg/day, and preferably about 1-30 mg/day depending on the patient, e.g. a human, and severity of the anxiety being treated.

EXAMPLE 1

(a)

Methyl -(2-methyl-2,3-dihydroxy)propionate

Methyl methacrylate (25 g) was added dropwise to a solution of OsO₄ (1 g) in acetone/water/t-butanol (9/1/1), stirring at 0° C. under a dry $N_2$ atmosphere. The mixture was warmed to room temperature and stirred for 12 hours. A solution of $KHSO_4$ (20 g) in water (100 ml) was added and the mixture stirred for 20 minutes, filtered through hyflo and adjusted to pH2 with 5N HCl. The solution was extracted with ethyl acetate (3×200 ml), dried over $MgSO_4$ and the solvent removed to give a brown oil. Distillation afforded the title compound 13.34 g. bp 110° C. @ 1.1 mmHg. $\delta_H$ (360 MHz, $CDCl_3$) 1.34 (3H, s, COH—$CH_3$), 3.52 (1H, d, J=10.0 Hz, CHH—OH), 3.78 (1H, d, J=10.0 Hz, CHH—OH), 3.79 (3H, s, $CO_2CH_3$), 4.08 (2H, brs, C—OH).

(b)

Methyl-2,2,4-trimethyldioxolane-4-carboxylate

Methyl (2-methyl-2,3-dihydroxy)propionate (30.33 g) and pyridinium para-toluenesulphonate (50 g) were combined together in a mixture of 2,2-dimethoxypropane and dichloromethane (1:1) (200 ml). The mixture was warmed to reflux a dry $N_2$ atmosphere for 18 hours, cooled to room temperature, washed with saturated $NaHCO_3$ solution (100 ml), dried over $MgSO_4$ and the solvent removed at reduced pressure to give a clear oil. Distillation afforded the title compound (24.47 g). b.p. 144° C.@ 1.0 mmHg. $\delta_H$(360 MHz, $CDCl_3$) 1.37 (3H, s, C—MeMe), 1.39 (3H, s, C—MeMe), 1.51 (3H, s, $CH_2C$—Me), 3.76 (3H, s, $OCH_3$), 3.78 (1H, d, J=10.0 Hz, CHH—O—C($CH_3$)$_2$), 4.38 (1H, d, J=10.0 Hz, CHH—O—(C$CH_3$)$_2$).

(c)

7-Choloro-5,6-dihydro-3-(5-(2,2,4-trimethyldioxolane)-1,2,4-oxadiazol-3-yl)5-methyl-6-oxo-4H-imidazo[1,5a][1,4]benzodiazepine 7-Chloro-5,6-dihydro-5-methyl-6-oxo-4H-imidazo [1,5a],[1,4]benzodiazepine-3-amide oxime (12.96 g) and 4A molecular sieve (15 g) were stirred together in THF (100 ml) under a dry $N_2$ atmosphere for 15 minutes. NaH (3 g of 80% dispersion in oil) was added and the solution stirred for a further 15 minutes. The mixture was then warmed to 50° C. and methyl 2,2,4-trimethyldioxolane 4-carboxylate (31.2 g) added over a period of five minutes. The mixture was then warmed to reflux for 90 minutes, cooled to room temperature, quenched with glacial acetic acid (3 ml), filtered through hyflo and dried over $MgSO_4$. Removal of solvent at reduced pressure gave a brown oil. Chromatography on silica gel using ethyl acetate as eluant afforded the title compound 8.05 g; m.p. 190° C. (dec). $\delta_H$(360 MHz, $CDCl_3$) 1.50 (3H, s, CMeMe), 1.52 (3H, s, CMeME, 1.81 (3H, s, $CH_2CCH_3$, 3.20 (3H, s, N—$CH_3$), 4.08 (1H, d, J=10.8 Hz, $CH_3$N—CHH—C=C), 4.47 (1H, d, J=14.4 Hz, CHH—O—C($CH_3$)$_2$), 4.61 (1H, d, J=10.8 Hz, $CH_3$N—CHH—C=C), 5.16 (1H, d, J=14.4 Hz, CHH—OC($CH_3$)$_2$), 7.34 (1H, dd, H-10, J=7.0, 1.0 Hz), 7.49 (1H, t, H-9, J=7.0 Hz), 7.57 (1H, dd, H-8, J=7.0, 1.0 Hz), 8.01 (1H, s, N—CH=N).

(d)

7-Chloro-5,6-dihydro-3-(5-(1,2-dihydroxyisopropyl)-1,2,4-oxadiazol-3-yl)-5-methyl-6-oxo-4H-imidazo[1,5a][1,4,]benzodiazepine 7Chloro-5,6-dihydro-3-(5-(2,2,4-trimethyldioxolane)-1,2,4-oxadiazol-3-yl)-5-methyl-6-oxo-4H-imidazo[1,5a][1,4]benzodiazepine (8.05 g) was dissolved in a mix of 80% acetic acid/acetone (150 ml) and warmed to reflux for 48 hours. The mixture was then cooled to room temperature and the solvent removed at reduced pressure. The residual oil was purified by chromatography in silica using 5% methanol in dichloromethane as eluant to afford the title compound 4.96 g; m.p. 229°-231° C. Found C, 52.23; H, 4.36; N, 17.45; $C_{17}H_{16}O_4N_5Cl$ requires C, 52.47; H, 4.25; N, 17.38%; $\delta_H$ (360 MHz, $CDCl_3$) 1.66 (3H, s, COH—$CH_3$), 3.21 (3H, s, N—$CH_3$), 3.72 (1H, d, J=10.8 Hz, CHH—OH), 4.15 (1H, d, J=10.8 Hz, CHH—OH), 4.49 (1H, d, J=14.4 Hz, $CH_3$N—CHH), 5.10 (1H, d, J=14.4 Hz, $CH_3$N—CHH), 7.35 (1H, d, J=7.2 Hz, H-10), 7.52 (1H, t, J=7.2 Hz, H-9), 7.6 (1H, d, J=7.2 Hz, H-8), 8.05 (1H, s, N—CH=N); m/z [M-H]+, 388 (20), 345 (30), 296 (10), 273 (100), 239 (30), 120 (30), 85 (10).

EXAMPLE 2

Tablets containing the following ingredients are manufactured in the usual manner:

|  | mg/tablet |
|---|---|
| Active ingredient | 1 |
| Lactose | 103 |
| Maize starch | 25 |
| Microcrystalline cellulose | 70 |
| Magnesium stearate | 1 |
| Total | 200 |

EXAMPLE 3

Capsules containing the following ingredients are manufactured:

|  | mg/capsule |
|---|---|
| Active ingredient | 1 |
| Lactose | 164 |
| Maize starch | 30 |
| Talc | 5 |
| Total | 200 |

The active ingredient lactose and maize starch are mixed in a mixer and then in a comminuting machine. The mixture is returned to the mixer, the talc is added thereto and mixed thoroughly. The mixture is filled by machine into hard gelatine capsules.

EXAMPLE 4

Injection solutions containing the following ingredients are manufactured:

|  | Per ml |
|---|---|
| Active ingredient | 0.5 mg |
| Benzyl alcohol | 0.015 ml |
| Propyleneglycol | 0.4 ml |
| Ethanol (95 percent) | 0.1 ml |
| Sodium benzoate | 48.8 mg |
| Benzoic acid | 1.2 mg |
| Water per injection q.s. ad | 1.0 ml |

For the manufacture of 10,000 ml of injection solution, 5 g of the active substance are dissolved in 150 ml of benzyl alcohol and 4000 ml of propylenegycol and 1000 ml of ethanol are added thereto. Then, 12 g of benzoic acid are dissolved in the above mixture and there is added thereto a solution of 488 g of sodium benzoate in 300 ml of water for injection. The solution obtained is brought up to a volume of 10,000 ml by addition of water for injection, filtered and filled into ampoules of suitable size; the residual volume of the ampoules is filled with nitrogen, the ampoules are sealed and sterilized for 30 minutes in an autoclave at 0.7 atmosphere.

EXAMPLE 5

Suppositories containing the following ingredients are manufactured:

|  | g/suppository |
| --- | --- |
| Active ingredient | 0.001 |
| Cocoa butter (m.p. 36-37°) | 1.255 |
| Carnauba wax | 0.044 |
| Total | 1.3 |

The cocoa butter and carnauba wax are melted in a glass or steel vessel, mixed thoroughly and cooled to 45°. Thereupon, there is added thereto the finely powdered active substance and the mixture is stirred until it is completely dispersed. The mixture is poured into suppository moulds of suitable size, left to cool, the suppositories are removed from the moulds and packed individually in wax paper or metal foil.

What is claimed is:

1. A coumpound of structural formula:

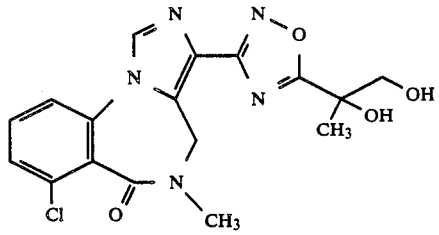

or a pharmaceutically acceptable salt thereof.

2. A pharmaceutical formulation for the treatment of anxiety comprising a pharmaceutical carrier and an anxiolytic amount of the compound of claim 1.

3. A method of treating anxiety comprising the administration of an effective anxiolytic amount of the compound of claim 1 to a patient in need of such treatment.

* * * * *